(12) United States Patent
Zilberman

(10) Patent No.: US 9,640,198 B2
(45) Date of Patent: May 2, 2017

(54) CONTROLLING A SYSTEM USING VOICELESS ALARYNGEAL SPEECH

(71) Applicant: BIOSENSE WEBSTER (ISRAEL) LTD., Yokneam (IL)

(72) Inventor: Israel Zilberman, Yokneam (IL)

(73) Assignee: Biosense Webster (Israel) Ltd. (IL)

( * ) Notice: Subject to any disclaimer, the term of this patent is extended or adjusted under 35 U.S.C. 154(b) by 95 days.

(21) Appl. No.: 14/041,271

(22) Filed: Sep. 30, 2013

(65) Prior Publication Data

US 2015/0095036 A1    Apr. 2, 2015

(51) Int. Cl.
| | |
|---|---|
| G10L 21/00 | (2013.01) |
| G10L 25/48 | (2013.01) |
| G10L 15/20 | (2006.01) |
| G06F 3/01 | (2006.01) |
| G10L 15/24 | (2013.01) |
| A61B 5/00 | (2006.01) |
| G10L 21/16 | (2013.01) |
| A61B 5/0488 | (2006.01) |

(52) U.S. Cl.
CPC ............. *G10L 25/48* (2013.01); *A61B 5/749* (2013.01); *G06F 3/015* (2013.01); *G10L 15/20* (2013.01); *G10L 15/24* (2013.01); *A61B 5/0488* (2013.01); *G10L 21/16* (2013.01)

(58) Field of Classification Search
CPC .......... G10L 25/48; G10L 15/24; G06F 3/015
See application file for complete search history.

(56) References Cited

U.S. PATENT DOCUMENTS

| 5,171,930 | A | 12/1992 | Teaney |
| 7,097,640 | B2* | 8/2006 | Wang ................ A61B 17/00 |
| | | | 381/110 |
| 8,098,423 | B2 | 1/2012 | Islam |
| 2007/0106501 | A1* | 5/2007 | Morita et al. ............ 704/200 |
| 2008/0010071 | A1* | 1/2008 | Callahan et al. ......... 704/270 |
| 2012/0232547 | A1* | 9/2012 | Cohen ........................ 606/34 |
| 2012/0299826 | A1 | 11/2012 | Moeller |

FOREIGN PATENT DOCUMENTS

WO PCT/US2003/001895     12/2003
WO  WO 2007/024983 A2      3/2007
(Continued)

OTHER PUBLICATIONS

Goldstein, E.A. et al. Design and Implementation of a Hands-Free Electrolarynx Device Controlled by Neck Strap Muscle Electromyographic Activity. IEEE Transactions on Biomedical Engineering, vol. 51, No. 2 Feb. 2004, pp. 325-332.

(Continued)

*Primary Examiner* — Richard Zhu

(57) ABSTRACT

Apparatus, including a sensor which is configured to be fixed to a neck of an operator of equipment in a location suitable for sensing a voiceless alaryngeal speech vibration generated by the operator during operation of the equipment, The apparatus further includes a processor which is configured to receive and process a signal output by the sensor so as to measure the voiceless alaryngeal speech vibration and so as to generate a control signal for the equipment responsively to the measured voiceless alaryngeal speech vibration.

10 Claims, 2 Drawing Sheets

(56) References Cited

FOREIGN PATENT DOCUMENTS

WO   PCT/US2008/082835      11/2008
WO   WO 2009/062061 A1       5/2009

OTHER PUBLICATIONS

Goldstein, E.A. et al. Training Effects on Speech Production Using a Hands-Free Electromyographically Controlled Electrolarynx. Journal of Speech, Language, and Hearing Research, vol. 50, Apr. 2007, pp. 335-351.
Goldstein, E., et al., "Design and Implementation of a Hands-Free Electrolarynx Device Controlled by Neck Strap Muscle Electromyographic Activity", IEEE Transactions on Biomedical Engineering, vol. 51, No. 2, Feb. 2004.
European Search Report for corresponding Application No. EP14186865.3 dated Feb. 23, 2015.

\* cited by examiner

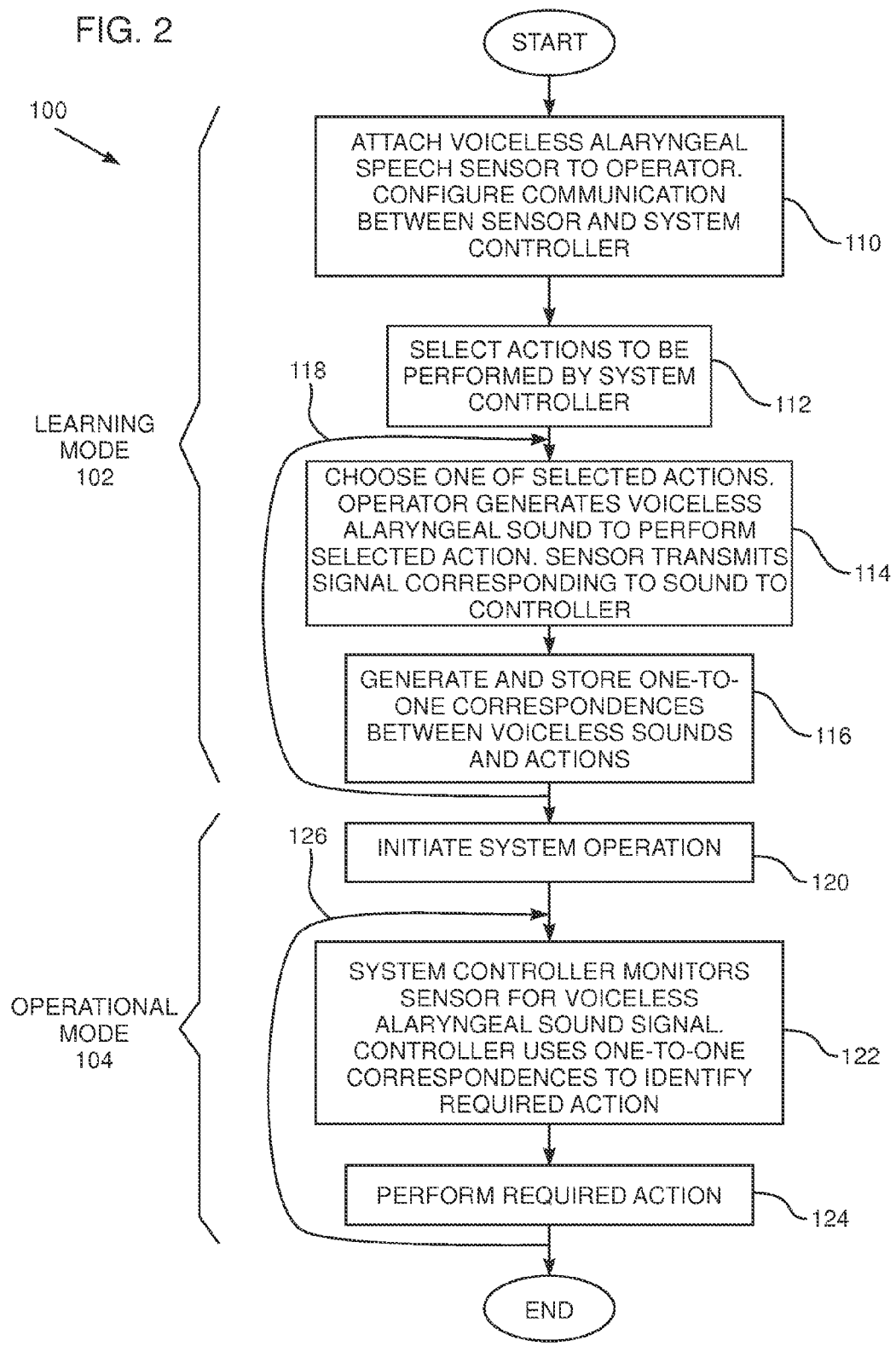

CONTROLLING A SYSTEM USING VOICELESS ALARYNGEAL SPEECH

FIELD OF THE INVENTION

The present invention relates generally to control of apparatus, and specifically to control of the apparatus using non-vocal vibrations.

BACKGROUND OF THE INVENTION

U.S. Pat. No. 8,098,423, to Islam, whose disclosure is incorporated herein by reference, describes a system and method for voice control of medical devices. The disclosure states that a medical device includes an insertable portion capable of being inserted into an orifice associated with a body of a patient. The disclosure further states that the insertable portion comprises an automated head unit capable of being manipulated in at least two axes of motion based at least in part on one or more control signals, and that voice control may be used for the manipulation.

PCT Application PCT/US2008/082835, to Mahapatra et al., whose disclosure is incorporated herein by reference, describes a steerable epicardial pacing catheter system that is placed via a subxiphoid process. The disclosure states that the invention may be used in the field of voice control over medical systems and devices of use in specialized electrophysiology procedures that employ subxiphoid access.

PCT Application PCT/SE2003/001895, to Brusell et al., whose disclosure is incorporated herein by reference, describes a method for producing simulated speech without requiring the use of naturally sounding speech, where movements and conditions are detected when a user performs speech movements. Ultrasonic signals are emitted from the outside mainly in a direction towards the mouth and/or throat area of the user and reflected ultrasonic signals are registered.

U.S. Pat. No. 5,171,930, to Teaney, whose disclosure is incorporated herein by reference, describes a voice-controlled musical device that is driven by an electroglottograph as an input to a controller. The electroglottograph (EGG) has a transducer in the form of a band that is located about the user's neck. The EGG converts the cycle of opening and closing of the vocal folds of the user's vocal chords into a clean electrical signal that the disclosure claims is particularly accurate with respect to pitch.

U. S. Patent Application 2012/0299826 to Moeller et al., whose disclosure is incorporated herein by reference, describes A human/machine (HM) interface that enables a human operator to control a corresponding machine using the geometric degrees of freedom of the operator's vocal tract. In one embodiment, the HM interface has an acoustic sensor configured to monitor, in real time, the geometry of the operator's vocal tract using acoustic reflectometry. A signal processor analyzes the reflected acoustic signals detected by the acoustic sensor, e.g., using signal-feature selection and quantification, and translates these signals into commands and/or instructions for the machine.

Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

SUMMARY OF THE INVENTION

An embodiment of the present invention provides apparatus, including:

a sensor, configured to be fixed to a neck of an operator of equipment in a location suitable for sensing a voiceless alaryngeal speech vibration generated by the operator during operation of the equipment; and a processor, configured to receive and process a signal output by the sensor so as to measure the voiceless alaryngeal speech vibration and so as to generate a control signal for the equipment responsively to the measured voiceless alaryngeal speech vibration.

In a disclosed embodiment the voiceless alaryngeal speech vibration consists of a group of different voiceless alaryngeal sound vibrations generated by the operator, and measuring the voiceless alaryngeal speech vibration includes distinguishing the voiceless alaryngeal sound vibrations within the group.

In a further disclosed embodiment the voiceless alaryngeal speech vibration consists of a group of different voiceless alaryngeal sound vibrations generated by the operator, and the processor is configured to store one-to-one correspondences between the group of different voiceless alaryngeal sound vibrations and a set of different control signals for the equipment selected by the operator.

In an alternative embodiment the equipment is configured to perform ablation on a heart of a patient.

In a further alternative embodiment the sensor includes an electromyographically controlled electrolarynx (EMG-EL).

There is further provided, according to an embodiment of the present invention, a method, including:

fixing a sensor to a neck of an operator of equipment in a location suitable for sensing a voiceless alaryngeal speech vibration generated by the operator during operation of the equipment; and receiving and processing a signal output by the sensor so as to measure the voiceless alaryngeal speech vibration and so as to generate a control signal for the equipment responsively to the measured voiceless alaryngeal speech vibration.

The present disclosure will be more fully understood from the following detailed description of the embodiments thereof, taken together with the drawings, in which:

BRIEF DESCRIPTION OF THE DRAWINGS

FIG. 2 is a flowchart showing steps performed in activating a sensor of the system of FIG. 1, according to an embodiment of the present invention;

DETAILED DESCRIPTION OF EMBODIMENTS

Overview

Figure 1:
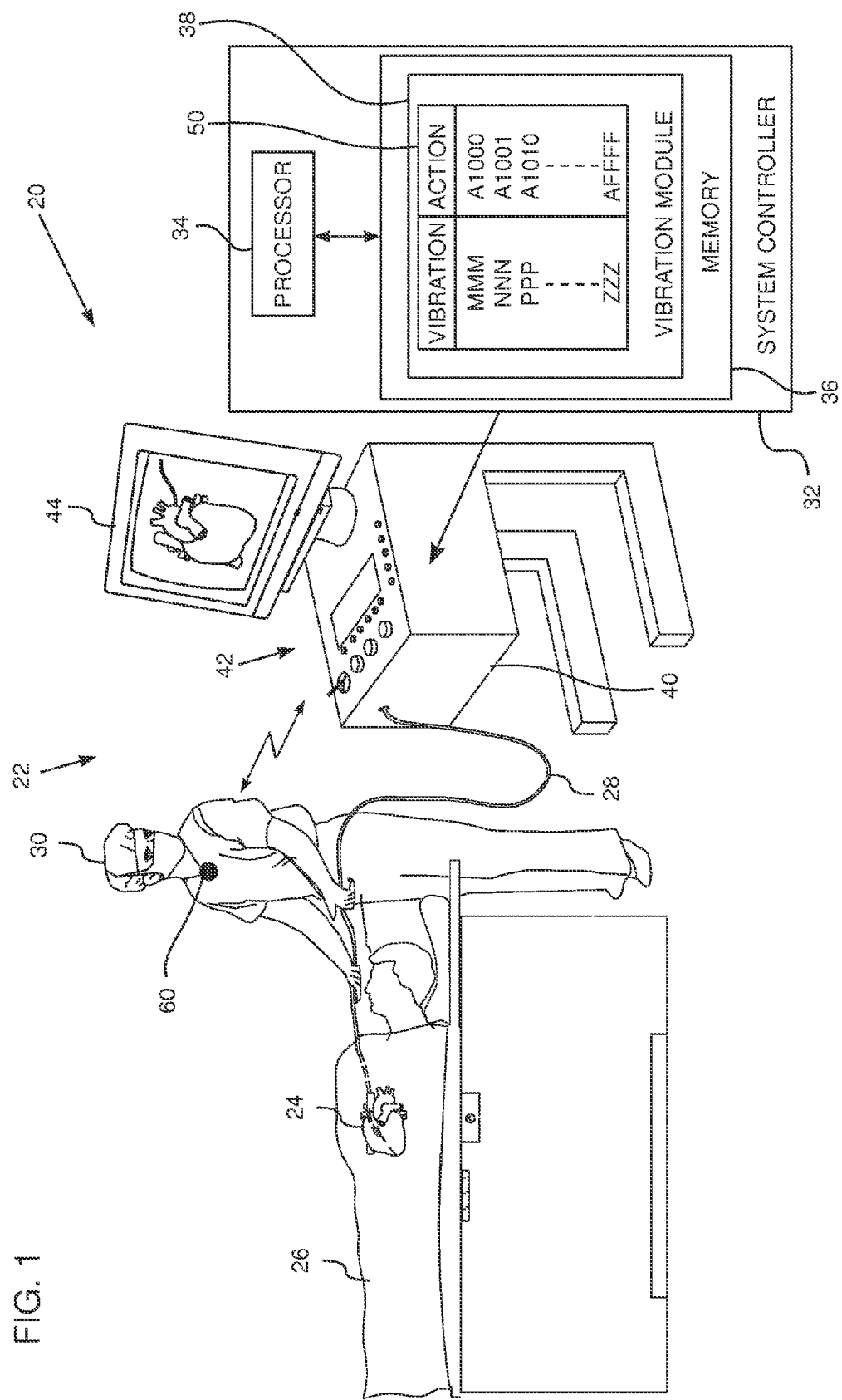
FIG. 1 is a schematic, pictorial illustration of a voiceless alaryngeal speech vibration detection and control system, according to an embodiment of the present invention.

An embodiment of the present invention comprises a system which enables an operator of equipment to control the equipment using voiceless alaryngeal speech vibrations generated by the operator. A sensor of the system, which is able to sense voiceless alaryngeal sound vibrations generated by the operator, is fixed to the neck of the operator in a location suitable for sensing the vibrations generating the voiceless sounds. The sensor is configured to generate signals in response to the vibrations, and a system processor is configured to receive and process the signals so as to measure the voiceless alaryngeal speech vibrations.

Typically, in a learning stage that is performed prior to an operational stage of the system, the operator generates a set of different voiceless alaryngeal sound vibrations or combination of such vibrations, and associates the vibrations, using respective signals generated by the sensor, in a one-to-one correspondence with respective control signals for the equipment. In the operational stage, the processor monitors the sensor for a signal generated in response to a specific operator voiceless alaryngeal sound vibration or combination of vibrations, and uses the one-to-one correspondence to determine a corresponding control signal to be applied to the equipment.

Use of voiceless alaryngeal speech vibrations to control equipment has a number of advantages. For example, during a medical procedure using multiple personnel a system operator may misinterpret the requests of the physician performing the procedure due to difficulties with language. Other factors, apart from language misunderstandings, such as indistinct enunciation by the physician or muffling of the physician's speech due to the physician's mask, may also cause miscommunication from the physician to the operator.

System Description

Reference is now made to FIG. 1, which is a schematic, pictorial illustration of a voiceless alaryngeal speech vibration detection and control system 20, according to an embodiment of the present invention. Voiceless alaryngeal speech vibrations and voiceless alaryngeal sound vibrations, both of which are used in system 20, are described below. In the following disclosure, system 20 is assumed to be implemented to partially control operations of equipment 22 that is used during a medical procedure, herein assumed to comprise an ablation procedure on a heart 24 of a patient 26. In some embodiments, equipment 22 may correspond to a CARTO® system available from Biosense Webster, Inc., 3333 Diamond Canyon Road, Diamond Bar, Calif. 91765. However, it will be appreciated that the description of this implementation using equipment 22 is by way of example, so that system 20 may be used to control other apparatus or equipment, including apparatus or equipment that is not necessarily associated with a medical procedure.

In system 20, a probe 28, comprised in equipment 22, is inserted into a chamber of heart 24 of patient 26. The probe may be used by an operator 30 of equipment 22, to perform ablation of a section of heart 24.

The functioning of system 20 is managed by a system controller 32, the controller being operated by a processor 34 communicating with a memory 36, wherein is stored software for operation of system 20. Memory 36 includes a vibration module 38 having a vibration-action table 50; the functions and properties of module 38 and of table 50 are described in more detail below.

Controller 32 is typically an industry-standard personal computer comprising a general-purpose computer processor. However, in some embodiments, at least some of the functions of the controller are performed using custom-designed hardware and software, such as an application specific integrated circuit (ASIC) or a field programmable gate array (FPGA). Controller 32 is typically installed in a console 40, and may be operated by operator 30 using controls 42 of the console; the controls typically include a pointing device, a touch screen, and/or a keypad which enable the operator to set parameters of system 20. A screen 44, connected to console 40, may display one or more different graphic user interfaces (GUIs) to operator 28, providing feedback to the operator to control system 20. The screen also displays results of the procedure to operator 30.

The software in memory 36 may be downloaded to the controller in electronic form, over a network, for example. Alternatively or additionally, the software may be provided on non-transitory tangible media, such as optical, magnetic, or electronic storage media.

A sensor 60 is attached to operator 30 in the vicinity of the operator's neck, and the sensor is configured to detect voiceless alaryngeal speech vibrations produced by the operator. Typically, sensor 60 is attached to operator 30 so that it is as close to the operator's pharynx as possible. For example, the sensor may be part of a necklace worn by the operator. Sensor 60 converts the voiceless alaryngeal speech vibrations it receives into electrical signals, and the electrical signals are transmitted to system controller 32. Typically, the signal transmission is implemented wirelessly, and in this case, part of the necklace described above may be configured as an antenna for the wireless transmission. Alternatively, the signal transmission may be via a cable coupled between the sensor and the system controller.

In the disclosure and in the claims, the terms voiceless alaryngeal speech vibrations and voiceless alaryngeal sound vibrations are to be understood as vibrations of the neck muscles of an operator of system 20 during respective mouthing of the speech and of the sounds. While mouthing of the speech or of the sounds, the operator does not use his/her voice. The vibrations are detectable by sensor 60, which typically comprises an electromyographically controlled electrolarynx (EMG-EL).

An EMG-EL that may be used as sensor 60 is described in a first article titled "Training Effects on Speech Production Using a Hands-Free Electromyographically Controlled Electrolarynx" by Goldstein et al., Journal of Speech, Language, and Hearing Research Vol. 50, pgs. 335-351 April 2007, and also in a second article titled "Design and Implementation of a Hands-Free Electrolarynx Device Controlled by Neck Strap Muscle Electromyographic Activity" by Goldstein et al., IEEE Transactions on Biomedical Engineering, Vol. 51, No. 2, February 2004. Both articles are incorporated herein by reference. Goldstein's EMG-EL uses a surface EMG electrode produced by DelSys Inc. of Boston Mass.

A description of how an operator of an EMG-EL may produce suitable alaryngeal speech vibrations and sound vibrations is provided in the first article cited above. As is explained there, a participant with normal neck anatomy is requested to not use their normal voice, but rather to hold their breath and mouth specific vowels, words, and sentences, in order to simulate conditions of a laryngectomy patient. In other words, the voiceless alaryngeal speech vibrations and sound vibrations referred to herein simulate the conditions of a laryngectomy patient when attempting to speak.

FIG. 2 is a flowchart 100 showing steps performed in activating and operating sensor 60, according to an embodiment of the present invention. Flowchart 100 is divided into two sections, a learning mode stage 102 wherein operator 30 "teaches" system 20 specific voiceless alaryngeal sound vibrations, collectively herein termed voiceless alaryngeal speech vibrations, generated by the operator, and an operational mode stage 104 wherein the system applies results of the learning section in order to operate system 20.

In an initial step 110 of the learning section, sensor 60 is attached to operator 28, substantially as described above, and the operator configures the sensor to communicate with system controller 32. The communication is herein assumed to be wireless communication. Typically, in order to configure the communication, the operator uses a configuration GUI, retrieved from vibration module 38, that is presented to the operator on screen 44.

In an action selection step 112, the operator selects actions that are to be performed by system 20 on detection of a specific voiceless alaryngeal sound vibration by sensor 60. Typically, during the procedure performed using equipment 22, there are a relatively large number of actions that the operator uses controls 42 to perform. Such actions include selecting a method of presentation of results of the procedure being performed, for example, in a graphical or tabular format. Other actions include enlarging/minimizing the view of a particular image, translating or rotating an image. For example, during an ablation procedure in the Carto system referred to above, the operator may use controls 42 to present a graphical and/or numerical display of the force and power applied during the ablation, and of the time during which ablation is applied. The operator may also use controls 42 to present a graphical and/or numerical display of temperatures of tissue being ablated.

Other examples of actions for equipment 22 using controls 42, and for other apparatus or equipment wherein system 20 is implemented, will be apparent to those having ordinary skill in the art, and all such actions are assumed to be included in the scope of the present invention.

In a learning step 114, the operator selects one of the actions chosen in step 112, and generates a voiceless alaryngeal sound vibration, or combination of such sound vibrations, that is to be used to perform the selected action. In response to the generated alaryngeal sound vibration, sensor 60 transmits a corresponding signal to controller 32. While the alaryngeal sound is being generated and the signal is being received, controller 32 may confirm to the operator, using a learning GUI retrieved from module 38 and displayed on screen 44, that a voiceless alaryngeal sound vibration signal is being received. Typically, after a length of time sufficient for the controller to be able to differentiate the alaryngeal sound vibration signal from other alaryngeal sound vibration signals, the controller indicates to the operator that the signal is a recognizable voiceless alaryngeal sound vibration signal that is distinguishable from other voiceless alaryngeal sound vibration signals. The length of time may be a preset length of time, typically of the order of seconds, which may be determined without undue experimentation on the part of the operator. Alternatively, for example after step 114 has been repeated a number of times, controller 32 may set the length of time adaptively.

In a correspondence step 116, controller 32 associates the recognizable voiceless alaryngeal sound vibration or combination of sound vibrations received in step 114 with the action selected by the operator in step 112. As shown by an arrow 118, steps 114 and 116 are reiterated by operator 30, so that controller 32 generates a set of one-to-one correspondences between a particular sound vibration or combination of sound vibrations and an action of equipment 22. Controller 32 stores the set of one-to-one correspondences in memory 36. The set may be stored in module 38 as table 50, or alternatively it may be stored by any other suitable method of storage.

In a first operational step 120, operator 30 initiates operation of equipment 22, and activates system 20. The activation of system 20 is typically performed by operator 30, using controls 42 and an operational GUI retrieved from module 38 and displayed on screen 44, to provide instructions to controller 32. The instructions enable the controller to accept signals from sensor 60 that have been generated in response to voiceless alaryngeal speech vibrations detected by the sensor. The instructions also enable the controller to access table 50.

In a second operational step 122, controller 32 monitors sensor 60, and checks periodically for signals from the sensor. If a signal is detected, the controller accesses the vibration-action table, and from the table determines the action corresponding to the signal.

In a perform action step 124, controller 32 implements the action identified in step 122. In some embodiments the controller may verify with the operator that a particular action is to be performed, such as by displaying a query on screen 44. (Typically such verification reduces the probability of system 20 performing unwanted actions.) The operator may confirm that the action is to be made, for example, by repeating the voiceless alaryngeal sound vibration, or combination of sound vibrations, detected in step 122, and/or by using other means known in the art, such as using one of controls 42.

As illustrated by an arrow 126, steps 122 and 124 are reiterated during the operational phase of system 20.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

I claim:

1. Apparatus for eliminating muffled speech caused by a physician's mask used by an operator during a medical procedure, comprising:
   a probe configured to be inserted into a patient's body by the operator, the probe being configured to be used by the operator for performing the medical procedure in the patient's body;
   a sensor, adapted to be fixed to a neck of an operator of equipment and configured for sensing a voiceless alaryngeal speech vibration generated by the operator during operation of the equipment;
   a screen for displaying one or more graphic user interfaces while the probe is being used by the operator in the patient's body and providing feedback to the operator during the medical procedure;
   a processor, configured to receive and process a signal output by the sensor during mouthing of muffled speech through the physician mask by the operator so as to measure the voiceless alaryngeal speech vibration and so as to generate a control signal indicative of a particular action to be taken by the equipment using the probe responsively to the measured voiceless alaryngeal speech vibration during the medical procedure, the particular action to be taken with the probe in the patient's body being verified by displaying a query on the screen for the operator to confirm using the one or more graphic user interfaces.

2. The apparatus according to claim 1, wherein the voiceless alaryngeal speech vibration comprise a group of different voiceless alaryngeal sound vibrations generated by the operator, and wherein measuring the voiceless alaryngeal speech vibration comprises distinguishing the voiceless alaryngeal sound vibrations within the group.

3. The apparatus according to claim 1, wherein the voiceless alaryngeal speech vibration comprises a group of different voiceless alaryngeal sound vibrations generated by the operator, and wherein the processor is configured to store one-to-one correspondences between the group of different voiceless alaryngeal sound vibrations and a set of different control signals for the equipment selected by the operator.

4. The apparatus according to claim 1, wherein the equipment is configured to perform ablation on a heart of a patient.

5. The apparatus according to claim 1, wherein the sensor comprises an electromyographically controlled electrolarynx (EMG-EL).

6. A method for eliminating muffled speech caused by a physician's mask used by an operator conducting a medical procedure, comprising the steps of:
providing a probe configured to be inserted into a patient's body by the operator, the probe being configured to be used by the operator for performing the medical procedure in the patient's body;
fixing a sensor to a neck of an operator of equipment, the sensor being configured for sensing a voiceless alaryngeal speech vibration generated by the operator during operation of the equipment;
displaying one or more graphic user interfaces on a screen while the probe is being used by the operator in the patient's body and providing feedback to the operator during the medical procedure;
receiving and processing a signal output by the sensor during mouthing of muffled speech through the physician mask by the operator so as to measure the voiceless alaryngeal speech vibration and so as to generate a control signal indicative of a particular action to be taken by the equipment using the probe responsively to the measured voiceless alaryngeal speech vibration during the medical procedure; and
verifying the particular action to be taken with the probe in the patient's body by displaying a query on the screen for the operator to confirm using the one or more graphic user interfaces.

7. The method according to claim 6, wherein the voiceless alaryngeal speech vibration comprises a group of different voiceless alaryngeal sound vibrations generated by the operator, and wherein measuring the voiceless alaryngeal speech vibration comprises distinguishing the voiceless alaryngeal sound vibrations within the group.

8. The method according to claim 6, wherein the voiceless alaryngeal speech vibration comprises a group of different voiceless alaryngeal sound vibrations generated by the operator, the method further comprising storing one-to-one correspondences between the group of different voiceless alaryngeal sound vibrations and a set of different control signals for the equipment selected by the operator.

9. The method according to claim 6, wherein the equipment is configured to perform ablation on a heart of a patient.

10. The method according to claim 6, wherein the sensor comprises an electromyographically controlled electrolarynx (EMG-EL).

* * * * *